United States Patent [19]
Mawhirt et al.

[11] Patent Number: 5,797,940
[45] Date of Patent: Aug. 25, 1998

[54] ADJUSTABLE SKIN INCISION DEVICE

[75] Inventors: James A. Mawhirt, Brooklyn, N.Y.;
Nikki S. Thompson, Freehold, N.J.

[73] Assignee: International Technidyne Corporation, Edison, N.J.

[21] Appl. No.: 866,172

[22] Filed: May 30, 1997

[51] Int. Cl.⁶ .................................................. A61B 17/32
[52] U.S. Cl. .................... 606/167; 606/170; 606/172; 606/181; 606/182
[58] Field of Search .......................... 606/167, 170, 606/172, 181, 182

[56] References Cited

U.S. PATENT DOCUMENTS

| | | | |
|---|---|---|---|
| 3,030,959 | 4/1962 | Grunert | 606/182 |
| 3,760,809 | 9/1973 | Campbell, Jr. | |
| 3,902,475 | 9/1975 | Begg et al. | |
| 4,203,446 | 5/1980 | Hofert et al. | 606/182 |
| 4,539,988 | 9/1985 | Shirley et al. | 606/182 |
| 4,628,929 | 12/1986 | Tengan et al. | 606/182 |
| 4,643,189 | 2/1987 | Mintz | |
| 5,133,730 | 7/1992 | Biro et al. | |
| 5,196,025 | 3/1993 | Ranalletta et al. | 606/182 |
| 5,212,879 | 5/1993 | Biro et al. | |
| 5,395,388 | 3/1995 | Schraga | |

*Primary Examiner*—Michael Powell Buiz
*Assistant Examiner*—Daphna Shai
*Attorney, Agent, or Firm*—Plevy & Associates

[57] ABSTRACT

A device for making an adjustably sized incision in skin. The device comprises a housing having a slotted opening; a blade disposed within the housing for making an incision in skin; a blade triggering mechanism disposed within the housing, for propelling the blade through the slotted opening of the housing a given distance to make an incision of a predetermined size in the skin; and incision size adjusting mechanism associated with the housing for selectively adjusting the size of the incision. The incision size adjusting mechanism includes a cam disposed within the housing, the cam being manually movable relative to the housing for allowing the size of the incision to be adjusted by variably limiting the given distance the blade is propelled through the slotted opening of the housing according to the cam's position relative to the housing. In one embodiment, the cam adjusts the size of the incision by varying the incision's depth into the skin to produce blood sample volumes which are selectively increased or decreased according to a selected depth of the incision. This feature makes the device especially suitable for making skin incisions in adults or children. In another embodiment, the cam adjusts the size of the incision by varying the incision's depth into the skin and the incision's length in the skin to produce blood sample volumes which are selectively increased or decreased according to a selected depth and length of the incision. This feature makes the device especially suitable for making skin incisions in infants and toddlers.

17 Claims, 7 Drawing Sheets

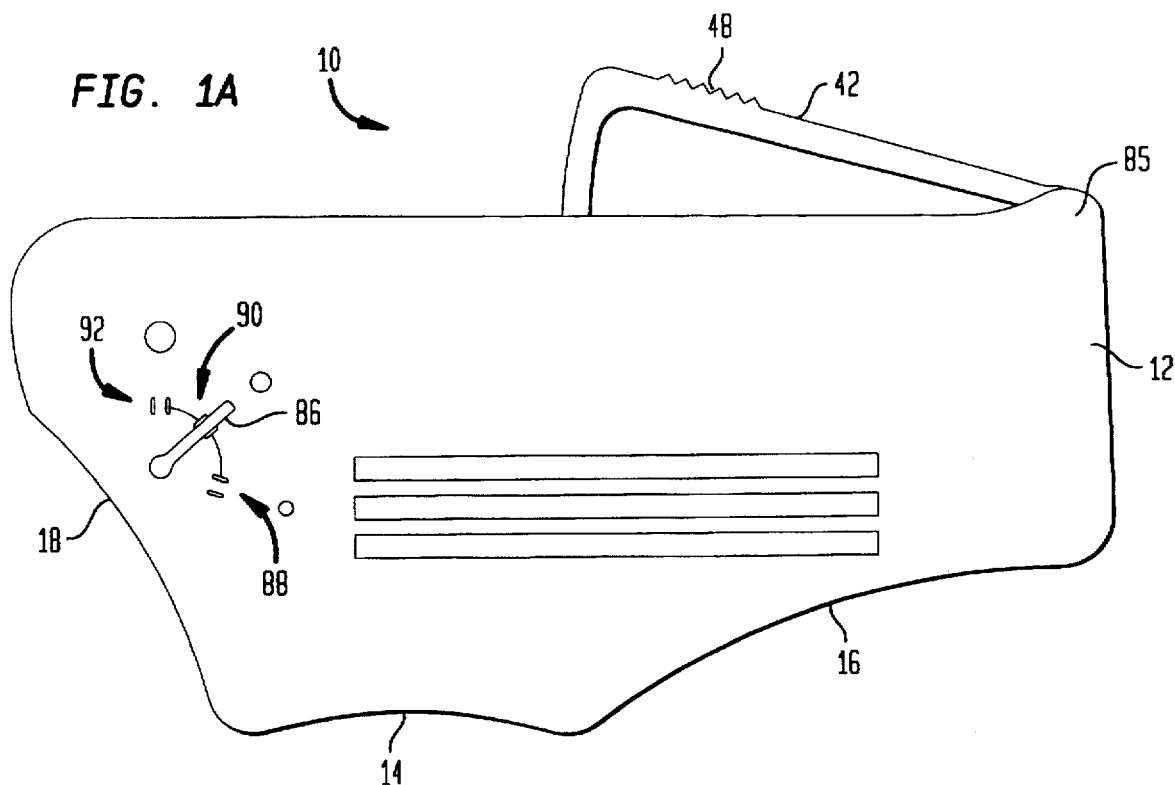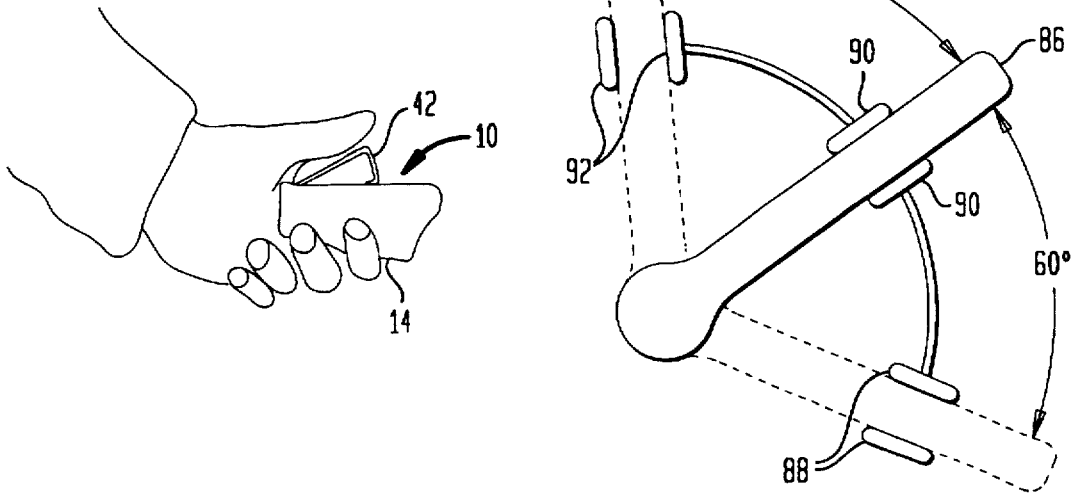

ADJUSTABLE SKIN INCISION DEVICE

FIELD OF THE INVENTION

The present invention relates to blood drop generation devices for making incisions in skin and more particularly to a blood drop generation making incisions of various depths in skin.

BACKGROUND OF THE INVENTION

Blood drop generation devices are well known in the art for providing blood samples which are used in performing various blood tests for preventative medicine and medical diagnosis. Such devices operate by creating a small puncture or incision in the skin in the skin of the fingertip or other area of the body such as the foot, arm, or leg.

Since most blood drop generation devices employ a lancet-like structure for puncturing or incising the skin, blood drop generation devices are often referred to as lancet devices. Many prior art lancet devices employ spring loaded cutting blades which are enclosed within a casing or housing. These devices are operated by placing the housing of the device against the skin and triggering the spring loaded cutting blade in the device. The potential energy stored within the spring accelerates the blade through an aperture in the housing and creates a uniform puncture or incision in the skin. The structural configuration of these devices enable the puncture or incision in the skin to be made in a controlled manner in terms of location, size, depth, and sterility. Since the blade is concealed within the housing, the patient is unable to view the blade prior to, or during the puncturing of the skin which reduces the patient's anxiety. Further, most recent designs of lancet devices include means for retracting the blade back into the housing after the puncture or incision has been made. Such a safety feature advantageously reduces the probability of a disease being spread through contact with the used blade of the device. This is an important feature since, deadly viruses such as AIDS and Hepatitis can spread from accidental punctures obtained from lancets used previously on an infected patient.

As already mentioned, the structural configuration of a lancet device enables it to puncture or incise the skin in a controlled manner in terms of location, size and depth. Devices which puncture the skin employ cutting blades which plunge perpendicularly into the skin to produce a skin incision of a predetermined depth. Such lancets are exemplified in U.S. Pat. No. 5,133,730 to Biro. In U.S. Pat. No. 5,133,730, a sharp blade is provided on a spring biased pivot arm which moves the blade out through an orifice in the lancet housing and then retracts the blade back into the housing. Although the blade is positioned on a pivot arm, the blade is directed perpendicularly, into the surface of the skin. The shape of the blade helps the blade enter the skin and make the needed incision. Other lancet devices that create plunge-type cuts are described in U.S. Pat. No. 3,760,809 to Cambell, Jr. and U.S. Pat. No. 5,395,388 to Schrage.

Lancet devices which incise the skin employ cutting blades which move in an arcuate motion or cutting blades which move simultaneously in a perpendicular and transverse motion. The lancet devices employing cutting blades that incise the skin in an arcuate manner are exemplified in U.S. Pat. No. 3,902,475 to Berg et al. The lancets in U.S. Pat. No. 3,902,475 produce skin incisions that vary in depth along the kength of the incision. Consequently, in order to obtain a requisite incision depth of between 1 and 5 mm, such a lancet devices must produce incisions that are relatively long and thus, less desirable.

The lancet devices employing cutting blades that incise the skin in a simultaneous perpendicular and transverse motion are capable of producing skin incisions which are uniform in depth along the entire length of the incision. Such a lancet device is described in U.S. Pat. No. 4,643,189 to Mintz. The simultaneous perpendicular and transverse motion of the cutting blade is accomplished by providing a unique cam configuration which controls the path of a pivoting arm that contains a cutting blade.

A disadvantage common to all of the above lancet devices involves is that none of these devices are capable of making incisions in skin which can be adjustably varied in depth or in depth and length. Thus, the blood samples produced by such lancet devices can not be adjusted for sample volume. This is significant in that different lancet devices must be employed when different blood sample volumes are desired.

Accordingly, there is need for a lancet device which is capable of providing adjustments in blood sample volumes.

SUMMARY

A device for making an adjustably sized incision in skin. The device comprises a housing having a slotted opening; a blade disposed within the housing for making an incision in skin; blade triggering and driving means disposed within the housing, for propelling the blade through the slotted opening of the housing a given distance to make an incision of a predetermined size in the skin; and incision size adjusting means associated with the housing for selectively adjusting the size of the incision.

The incision size adjusting means includes a cam disposed within the housing, the cam being manually movable relative to the housing for allowing the size of the incision to be adjusted by variably limiting the given distance the blade is propelled through the slotted opening of the housing according to the cam's position relative to the housing.

In one embodiment of the present invention, the cam adjusts the size of the incision by varying the incision's depth into the skin to produce blood sample volumes which are selectively increased or decreased according to a selected depth of the incision. This feature makes the device especially suitable for making skin incisions in adults or children.

In another embodiment of the present invention, the cam adjusts the size of the incision by varying the incision's depth into the skin and the incision'length in the skin to produce blood sample volumes which are selectively increased or decreased according to a selected depth and length of the incision. This feature makes the device especially suitable for making skin incisions in infants and toddlers.

BRIEF DESCRIPTION OF THE DRAWINGS

For a detailed understanding of the present invention, reference should be made to the following detailed description taken in conjunction with the accompanying drawings wherein:

FIG. 1A is a side elevational view of a lancet device in accordance with a first embodiment of the present invention;

FIG. 1B depicts an operator holding the lancet device of FIG. 1A;

FIG. 1C is an enlarged view of the selector lever of the lancet device of FIG. 1A;

DETAILED DESCRIPTION OF THE INVENTION

Figure 2A:
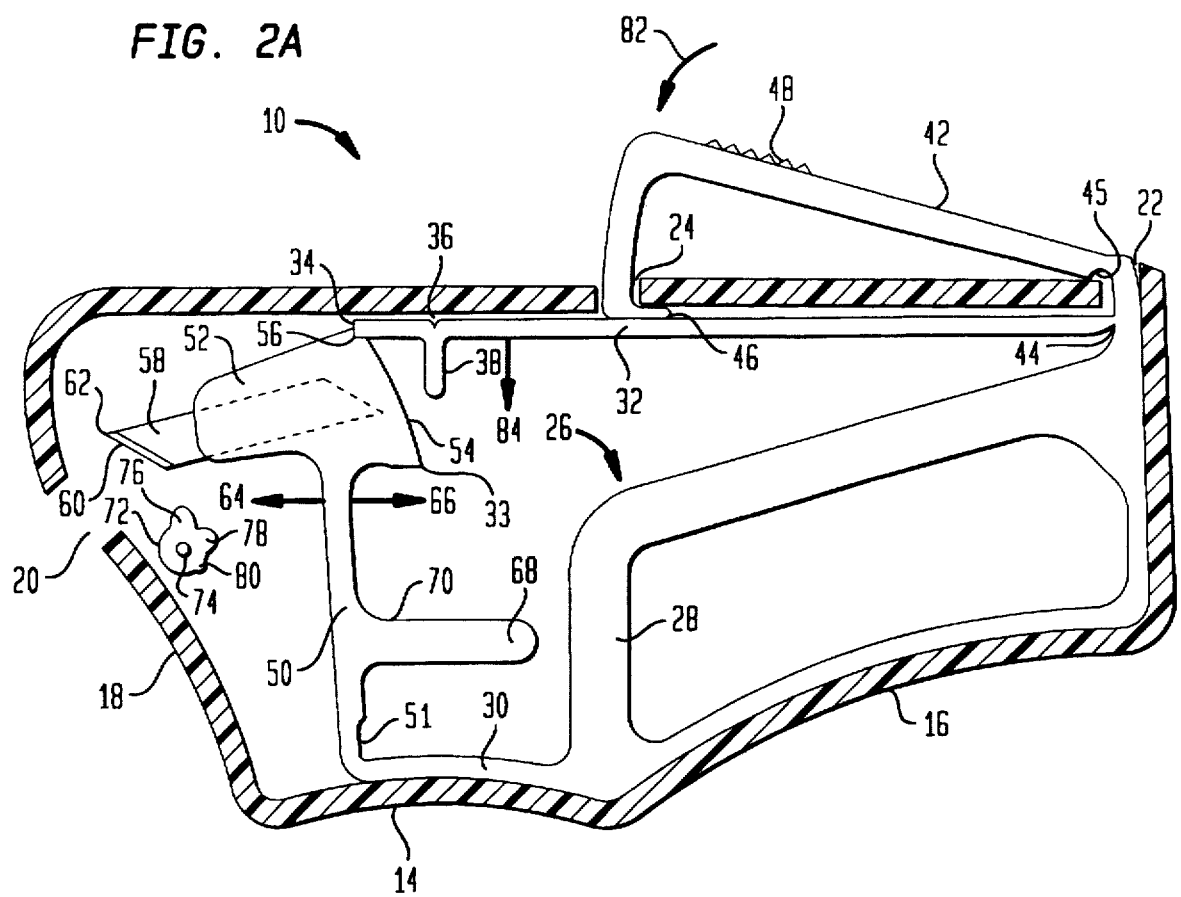
FIG. 2A is a cross-sectional side view of the lancet device of FIG. 1A in the armed position prior to activation.

Referring to FIG. 1A, a cutting depth-adjustable lancet device according to a first embodiment of the present invention is shown and denoted by the numeral 10. The lancet device 10 of the first embodiment, is especially suited for making skin incisions in adults and children since, the depth of the incision to be made by the lancet device 10 can be selectively adjusted, thereby providing a means for varying the volume of the blood sample to be obtained from the incision. This lancet device 10 includes a housing 12 which encloses a blade triggering mechanism having a thumb actuated trigger 42 that extends from inside the housing The housing 12 is designed with two ergonomic arcuate finger recesses 14, 16 and a third arcuate recess 18. As shown in FIG. 1B, the two finger recesses 14, 16 allow an operator to comfortably place the index and middle fingers on the bottom of the housing 12 and the thumb on the trigger 42 to grip and thereby operate the lancet device 10. The operator firmly places the third recess 18 flush against a patient's skin at the location where an incision is desired, such as the patient's finger. The lancet device 10 is then operated by squeezing the housing 12 and trigger 42 together to press the trigger 42 down into the housing 12. The depression of the trigger 42 irreversibly actuates the blade triggering mechanism located within the housing 12, and causes a blade to quickly emerge from the housing 12 a selected distance to puncture the patient's skin. The blade is then immediately retracted back into the housing 12 as will be explained further on. Once depressed, the trigger 42 cannot reactivate the blade triggering mechanism, therefore, the used blade, is locked permanently within the housing 12.

Referring again to FIG. 1A, a cutting depth selector lever 86 is provided on a side wall 85 of the housing 12 for selectively varying the volume of the blood sample obtained from an incision made in patient's skin. The selector lever 86 is coupled to a cam mechanism contained with the housing 12 that selectively adjusts the depth of the incision made by the lancet device 10 as will be explained in detail further on. Increasing or decreasing the depth of the incision respectively increases or decreases the volume of the blood obtained from the incision. The drawing of FIG. 1C, shows an enlarged view of the selector lever 86. As shown, a first, second and third pair of detents or protuberances 88, 90, 92 are provided on the sidewall 85 of the housing 12. The detent pairs 88, 90, 92 are disposed approximately 60 degrees apart from each other and allow the selector lever 86 to be properly positioned at one of three cutting depths. Other embodiments of the present invention can be adapted to provide less than two cutting depths, more than three cutting depths, or an infinitely variable number of cutting depths, if desired.

Referring now to FIG. 2A, a cross-sectional view through the housing 12 of the lancet device 10 revealing the earlier mentioned blade triggering mechanism in an armed position is shown and denoted by the numeral 26. The blade triggering mechanism 26 of this embodiment is based on lancet device of U.S. Pat. Nos. 5,133,730 and 5,212,879. Accordingly, the portions of these patents which are necessary for the understanding of the first embodiment of the present invention, are incorporated herein by reference. The blade triggering mechanism 26 is a unitarily molded plastic unit having a frame-like main body structure 28 which includes an extension member 30 that supports an arm link 50. A blade holder 52 is provided at the free end of the arm link 50. The blade holder 52 has a ramp surface 54 that extends from a notch or detent 56 formed therein. A metallic blade 58 is molded into the blade holder 52 such that a portion of the blade 58 extends out from the blade holder 52 toward a slotted opening 20 in the housing 12. The portion of the blade 58 extending out from the blade holder 52 includes a cutting edge 60 and a sharpened apex 62 which together, produces a scalpel-like incision when the blade 58 emerges from the housing 12 through the slotted opening 20. The other end of the arm link 50 is pivotally attached to the extension member 30 by a first living hinge 51 which enables the arm link 50 to pivot back and forth relative to the extension member 30 in the directions of arrows 64 and 66. The first living hinge 51 also biases the arm link 50 when it is pivoted and thus, causes the blade 58 to emerge from and retract back into the housing 12 through the slotted opening 20 when the lancet device 10 is operated. The arm link 50 also has a return lever 68, which extends in a generally perpendicular direction from an intermediate portion of the arm link 50. When a force is applied to the lever 68 at the area designated by numeral 70, the return lever 68 pivots the arm link 50 in the direction of arrow 66 thereby assisting the first living hinge 51 in retracting the blade 58 into the housing 12 after the incision is made.

The blade triggering mechanism 26 further includes a push rod 32 that has one end attached via a second living hinge 44 to the main body structure 28 which allows the push rod 32 to pivot relative thereto. The push rod 32 has a free end 34 that engages the detent 56 of the blade holder 52 in the armed position. The push rod 32 also includes a projecting member 38 that engages the return lever 68 of the arm link 50, the function of which will be described later, and a notch or detent 36 located marginally adjacent to the to the free end 34 thereof.

The trigger 42 mentioned earlier, is an L-shaped member having one end coupled to the main body structure 28 by a third living hinge 45. The junction where the third living hinge 45 and the main body structure merge 28, extends through an aperture 22 in the housing 12. The bent portion of the trigger 42 extends through second aperture 24 in the housing 12 and engages the push rod 32. A lip 46 is defined at the other end of the trigger 42 and prevents the bent portion thereof from being withdrawn through the second aperture 24 in the housing 12. The trigger 42 further includes a thumb gripping surface 48 which aids in prevention an operator's thumb from slipping off the trigger 42 during the operation of the lancet device 10.

As mentioned earlier, the lancet device 10 of the present invention includes a cam mechanism. The cam mechanism comprise a cam 72 that is affixed on a shaft 74 that extends through the sidewall 85 of the housing 12, and is coupled to the selector lever 86. 86. When the selector lever 86 is moved from one pair of detents to another, the cam rotates with the selector lever 86 via the shaft 74 to a different position.

Figure 2B:
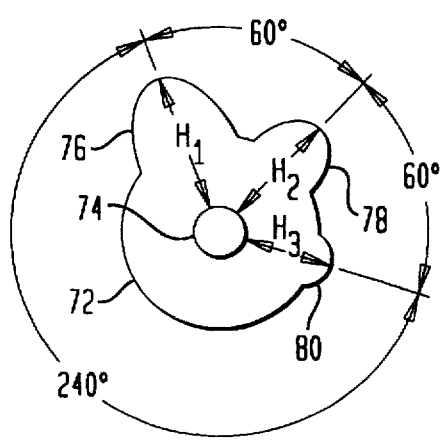
FIG. 2B is an enlarged view of the cam shown in FIG. 2A.

As best shown in FIG. 2B, the cam includes a first lobe 76, a second lobe 78 and a third lobe 80, each respectively having a different maximum height H1, H2, and H3, as measured from the shaft 74. The point of maximum height of the first lobe 76 is approximately 60 degrees from the point of maximum height of the second lobe 78. Similarly, the point of maximum height of the third lobe 80 is approximately 60 degrees from the point of maximum height of the second lobe 78. The points of maximum height of the first and third lobes 76, 78 are spaced approximately 240 degrees from each other.

Figure 2C:
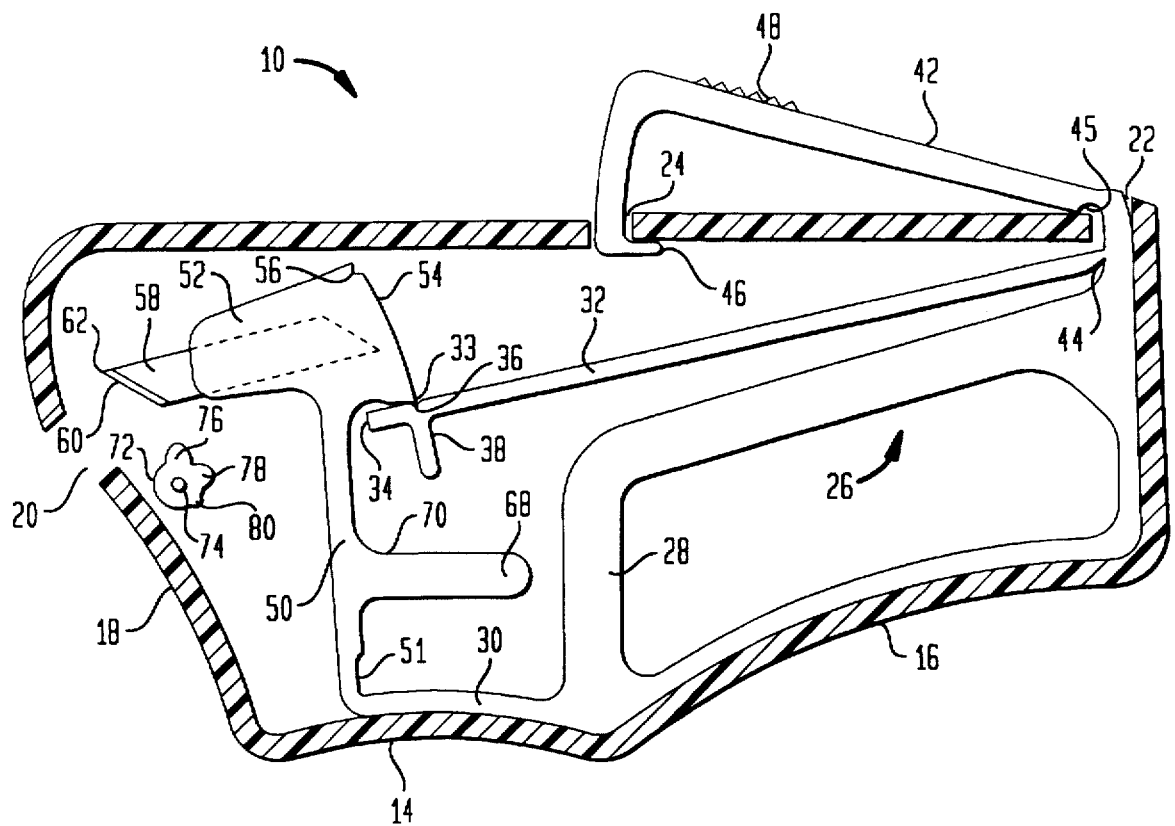
FIG. 2C is a cross-sectional side view of the lancet device of FIG. 1A, after the device has been activated.
Figure 2D:
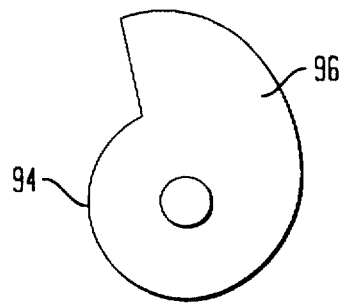
FIG. 2D is an enlarged view of another embodiment of the cam shown in FIG. 2B.
Figure 3A:
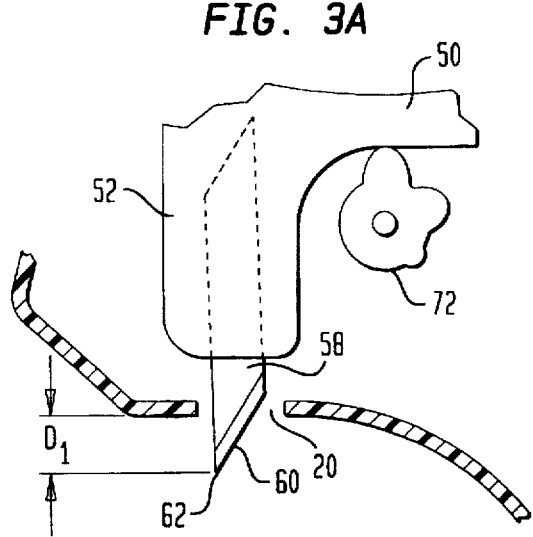
FIGS. 3A–3C are cross-sectional side views of the lancet device of FIG. 1A which depict how the cam mechanism varies the cutting depth of the device.
Figure 3B:
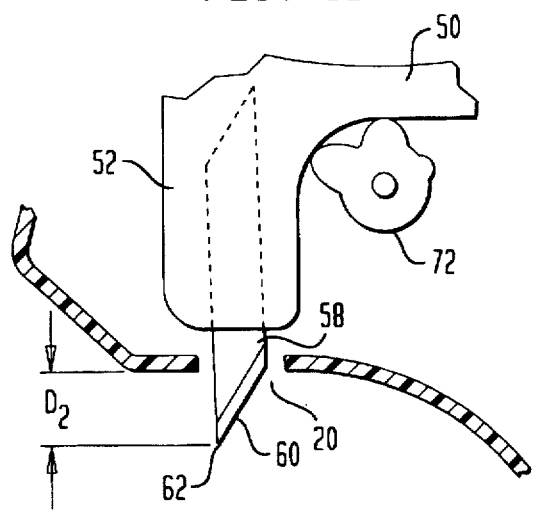
Figure 3C:
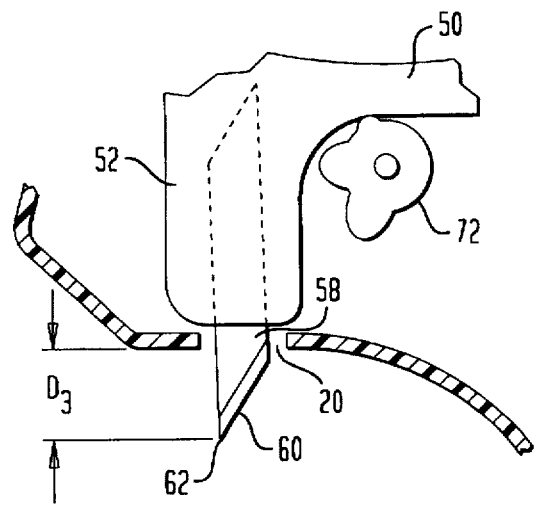

When the lancet device 10 of the first embodiment is assembled, it is set as shown in FIG. 2A in the armed position. This requires pivoting the arm link 50 in the direction of arrow 66 to engage the free end 34 of the push rod 32 with the detent 56 in the blade holder 52 during assembly of the device 10. This stresses the first living hinge 51 and thus, operates to lock the free end 34 of the push rod 32 in the detent 56 of the blade holder 52. When the trigger 42 is initially depressed in the direction of arrow 82 during the operation of the lancet device 10, the end of the trigger 42 having the lip 46 pushes the push rod 32 and flexes it since, the free end 34 of the push rod 32 is engaged with the detent 56 of the blade holder 52. The energy produced by the flexing of the push rod 32, when released, is channeled to push the blade holder 52. As the push rod 32 is flexed, its effective length decreases and causes the free end 34 thereof to disengage from the detent 56 in the blade holder 52. Once disengaged, the blade triggering mechanism 26 is irreversibly actuated in a snap-action motion. More specifically, the flexed push rod 32 simultaneously unflexes and pivots about the second living hinge 44 in the direction of the arrow 84, causing the free end 34 thereof to rapidly traverse the ramp surface 54, thereby pushing the blade holder 52 and pivoting the arm link 50 in the direction of the arrow 64. As the arm link 50 is pivoted, the apex 62 and the cutting edge 60 of the blade emerges from the housing 12 through the slotted opening 20. The cam 72 limits the pivotal motion of the arm link 50 to one of three different angular positions depending on which of the cam lobes has been selected to engage the arm link 50 and thus, limits the distance the blade 58 travels through the slotted opening 20 of the housing 12. This feature allows the operator of the device 10 to selectively choose one of three different incision depths in a patient's skin in accordance with a desired blood sample volume size. Accordingly, when the selector lever 86 shown in FIG. 1A is rotated between the first pair of detents 88, provided on the sidewall 85 of the housing 12, the cam 72 is oriented as shown in FIG. 3A, and creates an incision depth D1, which is the shallowest of the three possible incision depths, and hence produces the smallest blood sample volume. When the selector lever 86 is rotated between the second pair of detents 90, the cam 72 is rotated to the position shown in FIG. 3B which produces an incision depth D2, which is intermediate of the three possible incision depths and produces an intermediate sized blood sample volume. Similarly, when the selector lever 86 is rotated between the third pair of detents 92, the cam 72 is rotated to the position shown in FIG. 3C, which creates an incision depth D3, which is the deepest of the three possible incision depths and hence, produces the largest blood sample volume. One of ordinary skill in the art will recognize that the lancet device of the first embodiment can be easily modified to provide a lesser or greater number of cutting depths by varying the number of lobes on the cam 72. Moreover, an infinite number of cutting depths can be obtained in the first embodiment of the present invention, by providing a cam 94 as shown in FIG. 2D, that has a single lobe 96 with a height profile which progressively increases across the rotational range of the selector lever 86. Additionally, although the selector lever/cam mechanism depicted in the first embodiment provides cutting depth adjustments in approximately 120 degrees of selector lever rotation, the first embodiment of the present invention can be adapted to provide cutting depth adjustments in less than 120 degrees of selector lever rotation or up to approximately 360 degrees of selector lever rotation if desired. In any selected one of the three cutting depth positions, the snap-action motion of the blade triggering mechanism 26 is extremely rapid thereby reducing the patient's sensation of pain since, the apex 62 and cutting edge 60 of the blade 58 traverses the slotted opening 20 of the housing 12 in an extremely short period of time (1–5 milliseconds)

Once the incision is made in the patient's skin, the free end 34 of the push rod 32 has traverse the entire ramp surface 54 at which time, the projecting member 38 of the push rod 32 strikes the area 70 of the return lever 68, and reverses the pivoting direction of the arm link 50 to retract the blade 58 into the housing 12. This retraction of the blade 58 is aided by the plastic memory of the first living hinge 51 which biases the arm link 50 in the direction of arrow 66 when it is against the cam 72. Thus, immediately after the incision is implemented, the blade 58 retracted into the housing 12.

At the point where the projecting member 38 and the return lever 68 collide, the push rod 32 has expended most of its stored energy. Due to this loss of energy, and due to the plastic memory of the second living hinge 44, the push rod 32 starts to pivot back whereupon the detent or notch 36 of the push rod engages the edge 33 of the blade holder 52, which locks the arm link 50 in a final, unarmed position as shown in FIG. 2C. The plastic memory of the second living hinge 44 urges the push rod 32 up against the edge 33 of the blade holder 52. The plastic memory of the third living hinge 45 returns the trigger 42 to its original position. Consequently, depressing the trigger 42 again cannot reactivate the arm link 50 because the blade triggering mechanism 26 is not armed thereby, the lancet device can not be reused.

Figure 4A:
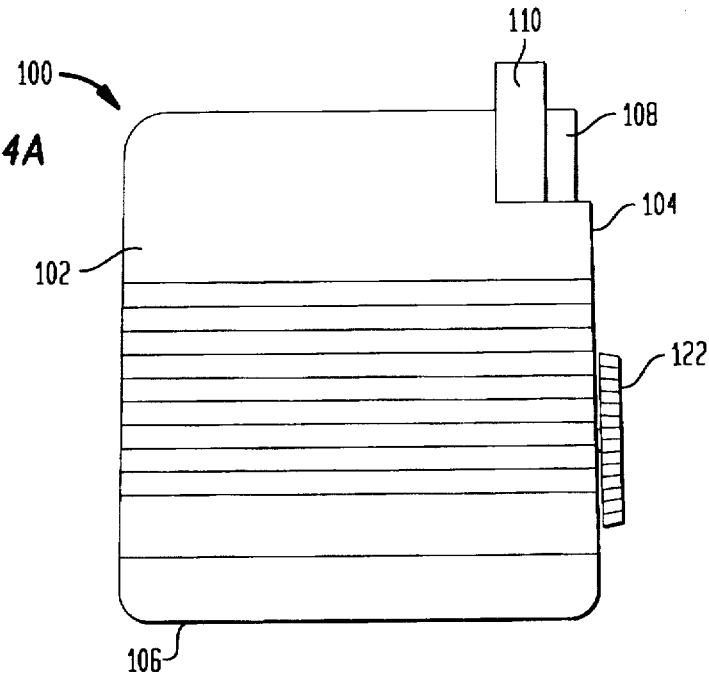
FIG. 4A is a side elevational view of a lancet device in accordance with a second embodiment of the present invention.

Referring now to FIG. 4A, a cutting depth-adjustable lancet device according to a second a second embodiment of the present invention is shown and denoted by the numeral 100. The lancet device lancet device 100 of the second embodiment, is especially suited for making skin incisions in infants and toddlers since, the depth and the length of selectively adjusted. The lancet device 100 of the second embodiment is based on the lancet device described in U.S. Pat. No. 4,643,189. Accordingly, the teachings of this patent as they apply to the present invention, are incorporated herein by reference.

Referring still to FIG. 4A, the lancet device 100 comprises a housing 102 with a pivoting base 106, which encloses a blade triggering mechanism which is activated by pushing a trigger 108 as will be explained. The trigger 108 is blocked by a detachable trigger guard 110 which is removed when the lancet device 100 is to be operated. An incision depth and length selector knob 122 is provided on an end wall 104 of the housing for selectively varying the depth and length of an incision made in an infant or toddler's skin. The selector knob 122 is coupled to a cam mechanism contained with the housing 102 that selectively adjusts the position of the base 106 relative to the housing 102, to vary the depth and length of the incision made by the lancet device 100 as will be explained below.

Figure 4B:
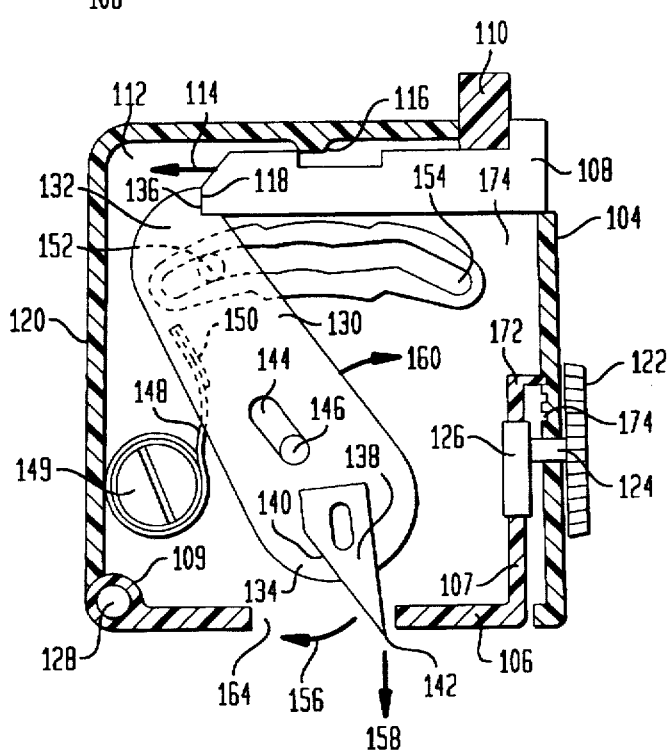
FIG. 4B is a cross-sectional side view of the lancet device of FIG. 4A in the armed position prior to activation.

Referring to FIG. 4B, a cross-sectional view through the housing 102 of the lancet device 100 revealing the earlier mentioned blade triggering mechanism in an armed position is shown. The housing 102 is molded from a suitable plastic and has a channel 112 which accommodates the trigger 108 of the blade triggering mechanism, which is a plunger-like device that is moveable in the direction of arrow 114. The channel 112 has a projecting boss 116 that holds the trigger 108 before activation of the lancet device 100. Thus to activate the lancet device 100, the operator must push the trigger 108 in the direction of the arrow 114. In order to prevent inadvertent operation, the trigger guard 110, which is a U-shaped member positioned in a space between the housing 102 and the trigger 108, prevents the trigger 108 from being moved in the direction of the arrow 114 when the guard 110 is emplaced on the housing 102.

The blade triggering mechanism further includes an arm link 130 having a detent or notch 136 at a first end 132 thereof and a triangular blade 138 with a cutting edge 140 and sharpened apex 142 disposed at a second end 134 thereof. The blade 138 may be secured to the arm link 130 by any conventional means and is scalpel-like in appearance and function. The arm link 130 includes an elongated aperture 144 which allows the arm link 130 to simultaneously rotate and reciprocate on a pivot shaft 146 define on an inner surface 172 of the housing 102. The arm link 130 also includes a cam follower 152 (shown in broken lines) disposed marginally adjacent to the first end 132 thereof. The cam follower 152 follows a specially profiled cam channel defined on the inner surface 172 of the housing 102, which causes the arm link 130 to simultaneously rotate and reciprocate according profile of the cam channel 154 when the device is activated. The detent 136 of the arm link 130, coact with the end 118 of the trigger 108 to retain the arm link 130 in a first position prior to device actuation. The arm link 130 also includes an arcuate flange 150 which accommodates one end of a torsion-type spring 148. The other end of the spring 148 is coupled to a diametrically slotted circular boss 149 defined on an inner surface 172 of the housing 102.

Figure 5:
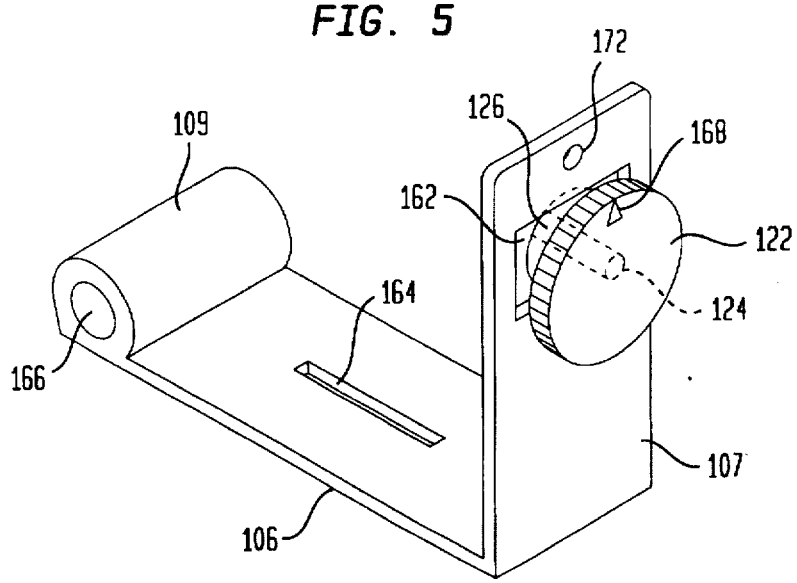
FIG. 5 is an enlarged view of the pivoting base and cam mechanism shown in FIG. 4B.

Referring now to FIG. 5 in conjunction with FIG. 4B, the base 106 of the housing 102 has an L-shaped profile which results from a vertical member 107 which extends therefrom. The end 109 of base 106 opposite to the vertical member 107 defmes a pivot aperture 166 which allows the base 106 to be pivotally coupled to the housing 102 via pivot pins 128 (only one of two is visible). With the base 106 assembled to the housing 102, the vertical member 107 is oriented adjacent to the interior surface of the end wall 104. The selector knob 122 is coupled to an eccentric cam 126 via a shaft 124 which extends through the end wall 104 of the housing 102, and captured thereby. An elongated slotted opening 164 is provided in the base 106 through which the blade 138 is directed, as will be explained. The vertical member 107 of the base 106 includes a cam window 162 which coacts with the cam 126 to pivot the base 106 up and down relative to the housing 102 when the cam 126 is rotated within the cam window 162. The free end of the vertical member 107 includes a bead 172 that engages a series of notches 174 defined on the inside of end wall 104 of the the housing 102 to provide a detent feature. This detent feature provides a positive and accurate positioning for the base 106. Additionally, this detent feature provides an audible 'click' sound to the rotation of the cam knob 122 when selecting alternate positions.

Figure 7:
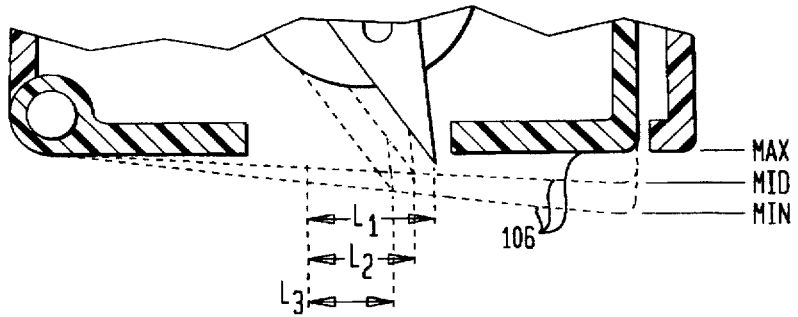
FIG. 7 is an enlarged cross-sectional side view of the lancet device of FIG. 4A which depicts how the pivoting base/cam mechanism varies the length of the incision.
Figure 6A:
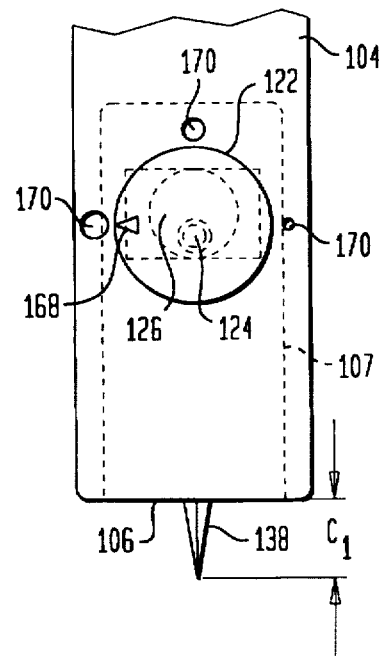
FIGS. 6A–6C are cross-sectional side views of the lancet device of FIG. 4A which depict how the pivoting base/cam mechanism varies the cutting depth of the device.
Figure 6B:
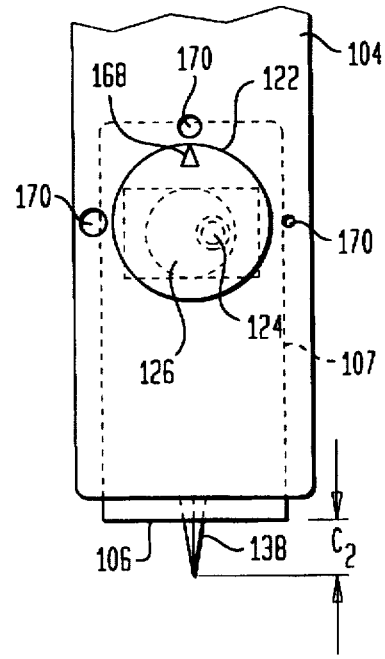
Figure 6C:
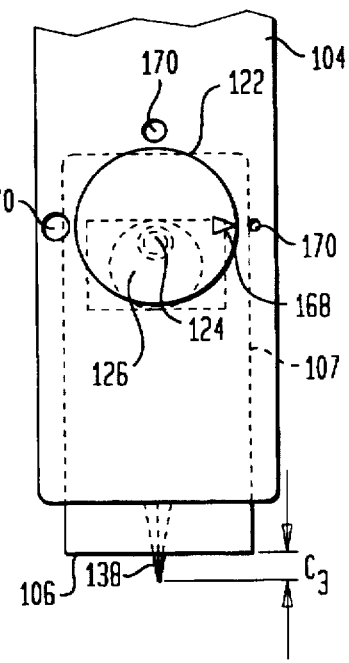

Referring to FIGS. 6A-6C, the selector knob 122 and the exterior surface of the end wall 104 of the housing 102 both include indicia 168, 170 which are used to accurately set the position of the base 106 relative to the housing 102. The indica on the end wall 104 are disposed approximately 90 degrees apart from each other to allow the base 106 to be pivoted up and down relative to the housing 102 into one of three positions which determines how far the blade 138 extends out of the slotted opening 164 of the base 106 during operation of the device 100. These three positions correspond respectively to three different cutting depths C1, C2, C3. As shown further in FIG. 7, the three position of the base 106 also provide correspondingly different incision lengths L1, L2, L3. In particular, the length of the incision shortens as the base 106 is pivoted down relative to the base 106 to produce a shallower incision depth.

Figure 6D:
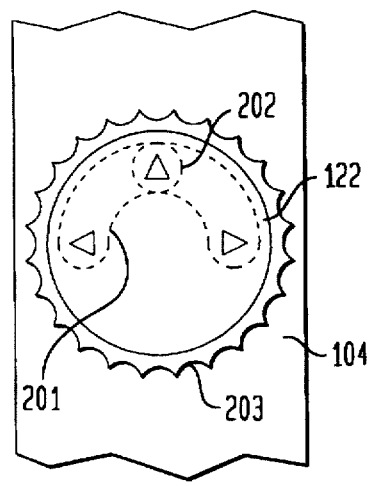
FIG. 6D is an enlarged view of a selector knob of the lancet device of the second embodiment.

In FIG. 6D, the outer surface of the end wall 104 includes a projection 202 which engages a circular slot section 201 on the back side of the selector knob 11 that provides a positive stop feature to prevent overtravel of the selector knob 122. The outer circumferential surface 203 of the selector knob 122 is textured to faciliate gripping of the knob 122. When operating the device, the middle position of the selector knob 122 is the start position with the other two positions providing ±90 degrees for adjustment.

Although the lancet device 100 of the second embodiment has been depicted with calibrations for three different settings for sample volume/cutting depth-length, it should be apparent to those skilled in the art that other embodiments of the lancet device 100 can be adapted to provide less than three settings, more than three settings, or an infinitely variable number of settings, if desired.

Referring again to FIG. 4B, when the lancet device 100 is assembled, the cutting edge 140 of the blade 138 is positioned above the slotted opening 164 of the base 106 but, is located within the housing 102 with the arm link 130 armed in a biased position via the spring 148. The cam follower 152 is positioned within the cam channel 154 and the end 118 of the trigger 108 is engaged with the detent 136 of the arm link 130 which prevents it from rotating.

Figure 4C:
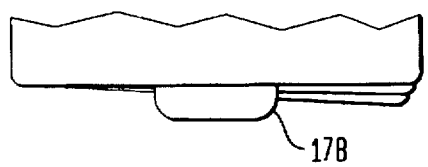
FIG. 4C depicts the approximate blade path of the lancet device of the second embodiment.

As the trigger 108 is pushed inwardly in the direction of the arrow, the trigger 108 pushes the first end of the arm link 130 toward the end wall or the housing 102 until the end of the trigger 108 disengages from the detent in the arm link 130. At this position, the energy stored in the spring 148 rotates the arm link 130 in the direction of arrow thus, causing the cutting edge of the blade 138 to move in the direction indicated by arrow 160, with the arm link's motion being controlled by the profile of the cam channel 154. In particular, the cam channel 154 causes the arm link 130 to first rotate in the direction of the arrow 160 and then move linearly in the direction of arrow 158 which causes the cutting edge of the blade 138 to immediately emerge from the housing 102 a set distance as determined by the selected position of the base 106 and produce an incision. With the cutting edge 140 of the blade 138 in the skin, linear movement in the direction of arrow 158 is halted, and rotation of the arm link 130 continues on for a predetermined number of degrees as controlled by the cam channel 154 which produces an incision of a uniform depth (the exact depth and length being determined by the position of the base 106). Then, the profile of the cam channel 154 causes the arm link 130 to move linearly in the direction opposite to the arrow 158 to withdraw the cutting edge 140 of the blade 138 from the skin and back into the housing 102 to produce a blade path 178 as shown in FIG. 4C.

Figure 4D:
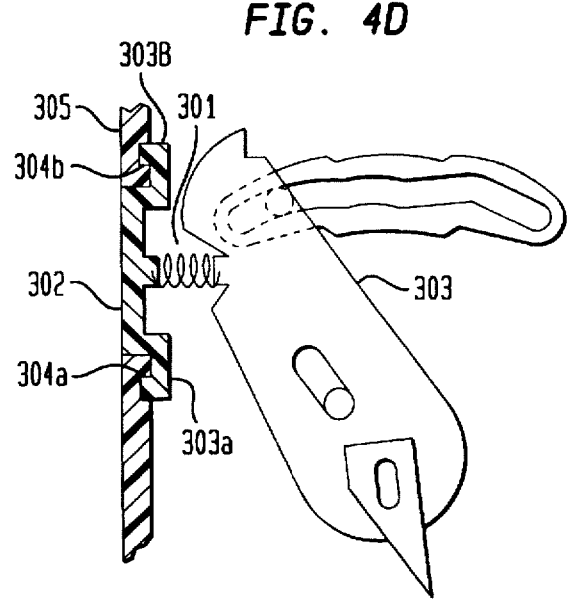
FIG. 4D depicts another embodiment of a spring used for rotating the arm link.

The torsion spring 148 depicted in FIG. 4B can be replaced by any spring configuration that would store energy and release that stored energy into the movement of the follower 130 riding in cam channel 154. For example, FIG. 4D depicts an embodiment where a compression spring 301 replaces the torsion spring of FIG. 4B. The compression spring 301 is held in place by a cover insert 302, and acts on the blade holder/follower 303. The cover insert 302 is retained by the spring 301 acting in conjunction with recessed tangs 303a and 303b which engage mating nests 304a and 304b in the wall 305 of the housing.

It will be understood that the embodiments described herein are merely exemplary and that a person skilled in the art may make many variations and modifications to the described embodiments utilizing functionally equivalent elements to those described. Any variations or modifications to the invention described hereinabove are intended to be included within the scope of the invention as defined by the appended claims.

What is claimed is:

1. A device for making an adjustably sized incision in skin, comprising:
   a housing having a slotted opening;
   a blade disposed within said housing for making an incision in skin;
   blade triggering means disposed within said housing, for propelling said blade through said slotted opening of said housing a given distance to make an incision of a predetermined size in the skin; and
   incision size adjusting means associated with said housing for selectively adjusting the size of the incision, wherein said incision size adjusting means includes a selector disposed externally on said housing and a cam which is coupled to said selector, said selector being movable relative to said housing for allowing the size of the incision to be manually selected and said cam operating to adjust the size of the incision when said selector is moved relative to said housing between a plurality of positions.

2. The device according to claim 1, wherein said housing includes externally located indicia which enables said selector to be accurately moved to a plurality of positions which correspond to a plurality of predetermined incision sizes.

3. A device for making an adjustably sized incision in skin, comprising:
   a housing having a slotted opening;
   a blade disposed within said housing for making an incision in skin;
   blade triggering means disposed within said housing, for propelling said blade through said slotted opening of said housing a given distance to make an incision of a predetermined size in the skin, and then retracting said blade through said slotted opening into said housing, said blade triggering means including a finger engageable trigger located external to said housing for acutating said blade triggering means; and
   incision size adjusting means associated with said housing for selectively adjusting the size of the incision, wherein said incision size adjusting means includes a selector disposed externally on said housing and a cam which is coupled to said selector, said selector being movable relative to said housing for allowing the size of the incision to be manually selected, and said cam operating to adjust the size of the incision when said selector is moved relative to said housing between a plurality of positions.

4. The device according to claim 3, wherein said housing includes externally located indicia which enables said selector to be accurately moved to a plurality of positions which correspond to a plurality of predetermined incision sizes.

5. The device according to claim 4, wherein said housing further includes detent detent means associated with said indicia that retains said selector in any selected one of said plurality of positions.

6. The device according to claim 3, wherein said incision size adjusting means includes a cam disposed within said housing, said cam being manually movable relative to said housing for allowing the size of the incision to be adjusted by variably limiting said given distance said blade is propelled through said slotted opening of said housing according to said cam's position relative to said housing.

7. A device for making an adjustably sized incision in skin, comprising:
   a housing having a slotted opening;
   a blade disposed within said housing for making an incision in skin;
   blade triggering means disposed within said housing, for propelling said blade through said slotted opening of said housing a given distance to make an incision of a predetermined size in the skin; and
   incision size adjusting means associated with said housing for selectively adjusting the size of the incision, wherein said incision size adjusting means includes a cam disposed within said housing, said cam being manually moveable relative to said housing for adjusting the size of the incision by variably limiting said given distance said blade is propelled through said slotted opening in said base according to the position of said cam relative to said housing.

8. The device according to claim 7, wherein said cam variably limits the depth of said incision into the skin to produce blood sample volumes which are selectively increased or decreased according to a selected depth of the incision.

9. The device according to claim 7, wherein said cam variably limits the depth of said incision into the skin and the length of said incision in the skin to produce blood sample volumes which are selectively increased or decreased according to a selected depth and length of the incision.

10. The according to claim 7, wherein said blade triggering means includes an arm link that propels said blade through said slotted opening of said housing, said cam engaging said arm link to variably limit said given distance said blade is propelled through said slotted opening of said housing via said arm link for varying the depth of said incision into the skin to produce blood sample volumes which are selectively increased or decreased according to a selected depth of the incision.

11. The device according to claim 7, wherein said housing has a base which defines a slotted opening and is moveable relative to said housing, said cam engaging and moving said base relative to said housing into a plurality of positions to variably limit said given distance said blade is propelled through said slotted opening in said base for varying the depth of said incision into the skin and the length of said incision in the skin to produce blood sample volumes which are selectively increased or decreased according to a selected depth and length of the incision.

12. A device for making an adjustably sized incision in skin, comprising:

a housing having a slotted opening;

a blade disposed within said housing for making an incision in skin;

blade triggering means disposed within said housing, for propelling said blade through said slotted opening of said housing a given distance to make an incision of a predetermined size in the skin, and then retracting said blade through said slotted opening into said housing, said blade triggering means including a finger engageable trigger located external to said housing for acutating said blade triggering means; and incision size adjusting means associated with said housing for selectively adjusting the size of the incision, wherein said incision size adjusting means includes a cam disposed within said housing, said cam being manually moveable relative to said housing for adjusting the size of the incision by variably limiting said given distance said blade is propelled through said slotted opening in said base according to the position of said cam relative to said housing.

13. The device according to claim 12, wherein said cam varies the depth of said incision to produce blood sample volumes which are selectively increased or decreased according to the selected depth of the incision.

14. The device according to claim 12, wherein said cam varies the depth of said incision into the skin and the length of said incision in the skin to produce blood sample volumes which are selectively increased or decreased according to the selected depth and length of the incision.

15. The device according to claim 12, wherein said blade triggering means includes an arm link that propels said blade through said slotted opening of said housing, said cam engaging said arm link to variably limit said given distance said blade is propelled through said slotted opening of said housing via said arm link for varying the depth of said incision into the skin to produce blood sample volumes which are selectively increased or decreased according to a selected depth of the incision.

16. The device according to claim 12, wherein said housing has a base which defines said slotted opening and is moveable relative to said housing, said cam engaging and moving said base relative to said housing into a plurality of positions to variably limit said given distance said blade is propelled through said slotted opening in said base for varying the depth of said incision into the skin and the length of said incision in the skin to produce blood sample volumes which are selectively increased or decreased according to a selected depth and length of the incision.

17. The device according to claim 16, wherein said base is pivotally attached to said housing to enable said base to move relative to said housing, said base including a window which coacts with said cam to to move said base relative to said housing into said plurality of positions.

* * * * *